United States Patent
Mannino et al.

(10) Patent No.: US 11,964,019 B2
(45) Date of Patent: Apr. 23, 2024

(54) COCHLEATES MADE WITH SOY PHOSPHATIDYLSERINE

(71) Applicants: RUTGERS, THE STATE UNIVERSITY OF NEW JERSEY, New Brunswick, NJ (US); MATINAS BIOPHARMA NANOTECHNOLOGIES, INC., Bedminster, NJ (US)

(72) Inventors: Raphael Mannino, Glen Gardner, NJ (US); Ruying Lu, New Providence, NJ (US)

(73) Assignees: Rutgers, The State University of New Jersey, New Brunswick, NJ (US); Matinas BioPharma Nanotechnologies, Inc., Bedminster, NJ (US)

( * ) Notice: Subject to any disclaimer, the term of this patent is extended or adjusted under 35 U.S.C. 154(b) by 0 days.

(21) Appl. No.: 16/904,824

(22) Filed: Jun. 18, 2020

(65) Prior Publication Data
US 2021/0038722 A1    Feb. 11, 2021

Related U.S. Application Data

(63) Continuation of application No. 15/811,040, filed on Nov. 13, 2017, now Pat. No. 10,716,860, which is a continuation of application No. 14/418,392, filed as application No. PCT/US2013/052756 on Jul. 30, 2013, now abandoned.

(60) Provisional application No. 61/835,825, filed on Jun. 17, 2013, provisional application No. 61/677,414, filed on Jul. 30, 2012.

(51) Int. Cl.
| | |
|---|---|
| *A61K 47/24* | (2006.01) |
| *A61K 9/127* | (2006.01) |
| *A61K 9/19* | (2006.01) |
| *A61K 31/12* | (2006.01) |
| *A61K 31/122* | (2006.01) |
| *A61K 31/685* | (2006.01) |
| *A61K 31/7036* | (2006.01) |
| *A61K 31/7048* | (2006.01) |
| *A61K 33/06* | (2006.01) |
| *A61K 45/06* | (2006.01) |
| *A61K 47/02* | (2006.01) |

(52) U.S. Cl.
CPC ............ *A61K 47/24* (2013.01); *A61K 9/1274* (2013.01); *A61K 9/1277* (2013.01); *A61K 9/19* (2013.01); *A61K 31/12* (2013.01); *A61K 31/122* (2013.01); *A61K 31/685* (2013.01); *A61K 31/7036* (2013.01); *A61K 31/7048* (2013.01); *A61K 33/06* (2013.01); *A61K 45/06* (2013.01); *A61K 47/02* (2013.01)

(58) Field of Classification Search
CPC .... A61K 47/24; A61K 9/1274; A61K 9/1277; A61K 9/19; A61K 31/12; A61K 31/122; A61K 31/685; A61K 31/7036; A61K 31/7048; A61K 33/06; A61K 45/06; A61K 47/02
See application file for complete search history.

(56) References Cited

U.S. PATENT DOCUMENTS

| | | | |
|---|---|---|---|
| 4,663,161 A | 5/1987 | Mannino et al. | |
| 5,554,382 A | 9/1996 | Castor | |
| 6,660,504 B2 | 12/2003 | Yamane et al. | |
| 6,663,885 B1 | 12/2003 | Hager et al. | |
| 8,642,073 B2 | 2/2014 | Mannino et al. | |
| 9,370,572 B2 | 6/2016 | Mannino et al. | |
| 9,775,907 B2 | 10/2017 | Mannino et al. | |
| 10,716,860 B2 | 7/2020 | Mannino et al. | |
| 2002/0106744 A1 | 8/2002 | Yamane et al. | |
| 2003/0054027 A1 | 3/2003 | Unger | |
| 2003/0219473 A1* | 11/2003 | Zarif | A61K 9/1274 514/420 |
| 2004/0120997 A1 | 6/2004 | Panzner et al. | |
| 2004/0146551 A1 | 7/2004 | Mannino et al. | |
| 2005/0008686 A1 | 1/2005 | Mannino et al. | |
| 2005/0013854 A1* | 1/2005 | Mannino | A61K 31/60 435/458 |
| 2005/0013855 A1 | 1/2005 | Gould-Fogerite et al. | |
| 2005/0118241 A1* | 6/2005 | Landschaft | A61P 31/00 514/5.5 |
| 2010/0239521 A1* | 9/2010 | Mozafari | A61K 9/107 530/331 |
| 2011/0256214 A1 | 10/2011 | Martin et al. | |
| 2015/0140074 A1 | 5/2015 | Mannino et al. | |

(Continued)

FOREIGN PATENT DOCUMENTS

| | | | |
|---|---|---|---|
| EP | 1223222 A1 | 7/2002 | |
| EP | 2689775 A1 | 1/2014 | |

(Continued)

OTHER PUBLICATIONS

Google_scholar_search_Jan. 25, 2022_phosphatidylserine_cochleate_drug (Year: 2022).*
Google_scholar_search_Jan. 25, 2022_phosphatidylserine_cochleate_drug_mannino (Year: 2022).*
International Search Report dated Dec. 6, 2013 from International Application No. PCT/US2013/052756, pp. 1-2.

(Continued)

*Primary Examiner* — Michael P Cohen
(74) *Attorney, Agent, or Firm* — Foley Hoag LLP; Amy E. Mandragouras; Ariana D. Harris

(57) ABSTRACT

Unpurified or low pure soy phosphatidylserine is used to make cochleates. The cochleates contain about 40-74% soy phosphatidylserine, a multivalent cation and a biological active. A preferred cochleate contains the antifungal agent amphotericin B.

13 Claims, 11 Drawing Sheets

(56) References Cited

U.S. PATENT DOCUMENTS

2015/0147380 A1    5/2015    Mannino et al.
2018/0185491 A1    7/2018    Mannino et al.

FOREIGN PATENT DOCUMENTS

| | | |
|---|---|---|
| JP | H0550062 A | 3/1993 |
| JP | 2005112731 A | 4/2005 |
| JP | 2010235520 A | 10/2010 |
| WO | 1991/002517 A1 | 3/1991 |
| WO | 93/11777 A1 | 6/1993 |
| WO | 1994/12156 A1 | 6/1994 |
| WO | WO-94/12155 A1 | 6/1994 |
| WO | 1996/025147 A1 | 8/1996 |
| WO | 2002/085337 A1 | 10/2002 |
| WO | 2003/082209 A2 | 10/2003 |
| WO | 2004/012709 A1 | 2/2004 |
| WO | 2004/037271 A1 | 5/2004 |
| WO | 2004/041247 A2 | 5/2004 |
| WO | 2004064805 A1 | 8/2004 |
| WO | 2004/091578 A2 | 10/2004 |
| WO | 2007/117509 A2 | 10/2007 |
| WO | 2010/091090 A1 | 8/2010 |
| WO | WO-2014/022414 A1 | 2/2014 |

OTHER PUBLICATIONS

Zayas et al., "Pilot Scale Production of the Vaccine Adjuvant Proteoliposome Derived Cochleates (AFCo1) from Neisseria Meningitidis Serogroup B," BMC Immunology 2013, 14(Suppl 1):S4, pp. 1-5.

International Search Report dated Feb. 10, 2016 from International Application No. PCT/US2013/052756, pp. 1-9.

Chinese Office Action and Search Report dated Feb. 21, 2017 for Chinese Patent Application No. 201380051033.2, 24 pages (including English translation).

Japanese Office Action dated May 23, 2017 for Japanese Application No. 2015-525517, 10 pages (including English translation).

BioDelivery Sciences International, Inc., "New BioGeode(TM) Cochleates Could Make Healthy Nutrients More Available in Processed Foods", Sep. 30, 2003, PR Newswire Association LLC, 2 pages.

First Examination Report dated Nov. 21, 2019 for Indian Application No. 1083/CHENP/2015, 8 pages.

Duzgunes et al. (1981). "Calcium- and Magnesium-Induced Fusion of Mixed Phosphatidylserine/Phosphatidylcholine Vesicles: Effect of IOn Binding." The Journal of Membrane Biology, 59:115-125.

Extended EP Search Report dated Feb. 10, 2016 from EP Application No. 13826076.5, pp. 1-9.

Maiskiy V.V. "Elementary Pharmacology", 2009, p. 422.

\* cited by examiner

COCHLEATES MADE WITH SOY PHOSPHATIDYLSERINE

RELATED APPLICATIONS

The present application is a continuation of U.S. application Ser. No. 15/811,040 (Allowed) filed 13 Nov. 2017, which is a continuation of U.S. application Ser. No. 14/418,392 filed 29 Jan. 2015, which is a U.S. National Phase application of PCT/US2013/052756 filed 30 Jul. 2013, which claims priority to U.S. Provisional Application No. 61/677,414 filed on Jul. 30, 2012 and U.S. Provisional Application No. 61/835,825 filed Jun. 17, 2013, the entire contents of each aforementioned application are incorporated herein by reference.

FIELD OF THE INVENTION

The present invention relates to the ability of unpurified or low purity (40-74% by weight) soy-based phosphatidylserine (PS) to prepare cochleates, methods of preparing drug-cochleates from soy-based PS and the use of this drug-loaded cochleate as a pharmaceutical treatment.

BACKGROUND OF THE INVENTION

Cochleate delivery vehicles are a broad-based technology for the delivery of a wide range of bioactive therapeutic products. Cochleate delivery vehicles are stable phospholipidation precipitates composed of simple, naturally occurring materials, for example, phosphatidylserine and calcium.

The bilayer structure of cochleates provides protection from degradation for associated, or "encochleated," molecules. Since the entire cochleate structure is a series of solid layers, components within the interior of the cochleate structure remain substantially intact, even though the outer layers of the cochleate may be exposed to harsh environmental conditions or enzymes. This includes protection from digestion in the stomach.

Taking advantage of these unique properties, cochleates have been used to mediate and enhance the oral bioavailability of a broad spectrum of important but difficult to formulate biopharmaceuticals, including compounds with poor water solubility, protein and peptide drugs, and large hydrophilic molecules. For example cochleate-mediated oral delivery of amphotericin B, large DNA constructs/plasmids for DNA vaccines and gene therapy, peptide formulations, and antibiotics such as clofazimine has been achieved.

Cochleates can be stored in cation-containing buffer, or lyophilized to a powder, stored at room temperature, and reconstituted with liquid prior to administration. Lyophilization has no adverse effects on cochleate morphology or functions. Cochleate preparations have been shown to be stable for more than two years at 4° C. in a cation-containing buffer, and at least one year as a lyophilized powder at room temperature.

Cochleates can be prepared by several methods, such as trapping or hydrogel methods (International Application Publication No. WO 03/082209, the entire content of which is incorporated herein by reference).

Soy PS is sold in health food stores as a nutritional supplement. Non-purified (40%) PS has been used and studied as a nutritional supplement and as a component that has a beneficial effect on enhancing the brain functions in elderly people (Villardita C et al., *Clin. Trials J.* 24, 1987, 84-93).

Although non-purified soy PS (NSPS) has been sold and studied on patients, NSPS (or low purity PS) has never been used to make cochleates and to deliver a drug using these cochleates. As previously disclosed in WO 03/082209, NSPS does not form cochleates and that a purification process is needed to enhance the NSPS in the content of PS, until at least about 75% by weight of PS is reached, such percentage allowing the formation of cochleates.

SUMMARY OF THE INVENTION

It has been unexpectedly found that NSPS or low purity soy-based PS (40-74% by weight) can still form cochleates.

Briefly, in accordance with the present invention, improved lipid based cochleates are made by using non-purified or low purity soy phosphatidylserine as the lipid source. The improved cochleates contain soy phosphatidylserine in an amount of about 40%-74% (preferably 45-70%, more preferably 45-55%) by weight of the lipid. The improved cochleates can be empty or loaded cochleates. Loaded cochleates can contain any biological actives or combination of biological actives such as, for example, a protein, a small peptide, a polynucleotide, an aminoglycoside, an antiviral agent, an anesthetic, an antibiotic, an antifungal, an anticancer, an immunosuppressant, a steroidal anti-inflammatory, a non-steroidal anti-inflammatory, a tranquilizer, a nutritional supplement, an herbal product, a vitamin or a vasodilatory agent. Of particular interest in practicing the present invention, antifungal agents or antibiotic agents are loaded into the present soy-based phosphatidylserine cochleates to provide a cost effective and improved antifungal drug/antibiotic drug with reduced toxicity. Preferred antifungal agents include amphotericin-B and nystatin. Preferred antibiotic agents include an aminoglycoside and amikacin.

The improved lipid based cochleates of the present invention can be made by a method comprising the steps of: (a) preparing liposomes in an aqueous medium wherein the liposomes have (i) a lipid bilayer comprising soy-based phosphatidylserine in an amount of about 40%-74% (preferably 45-70%, more preferably 45-55%) by weight of the lipid bilayer and (ii) a load of a biological active; (b) adding a multivalent cation to the suspension of liposomes of (a) to form the soy phosphatidylserine/biological active cochleates; and (c) collecting the soy-based phosphatidylserine/biological active cochleates.

The present invention also teaches that the soy phosphatidylserine/biological active cochleates can be administered to patients with fungal infections or with bacterial infections. The present soy phosphatidylserine/biological active cochleates are conveniently administered orally even in the treatment of systemic fungal infections of immune compromised patients. The present phosphatidylserine/biological active cochleates are also administered parenterally, or by other means of administration. The preferred biological active is amphotericin-B, curcumin, and amikacin.

DETAILED DESCRIPTION OF THE INVENTION

Figure 1:
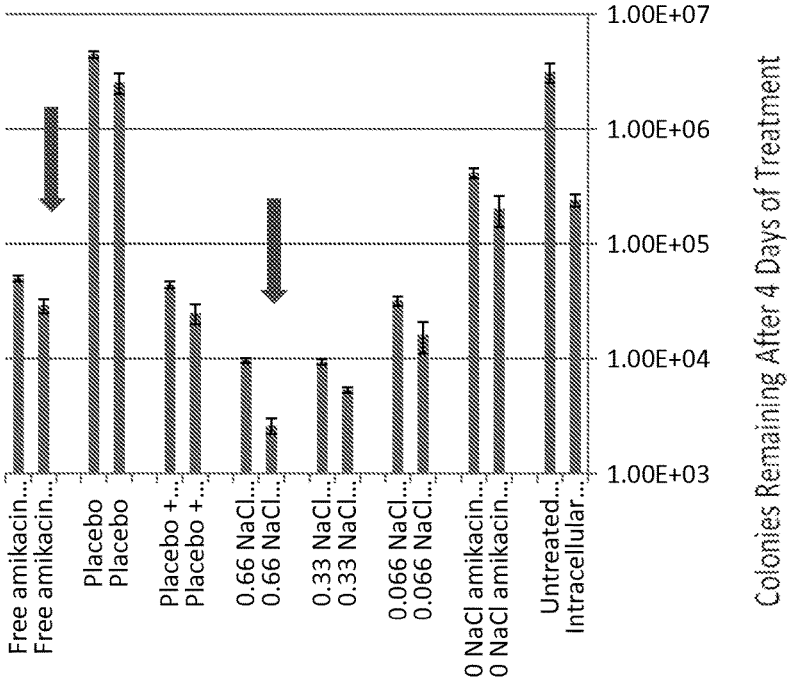
FIG. 1 shows amikacin cochleate in vitro study against MAC 101 and MAC 109 in mouse peritoneal macrophage.
Figure 1:
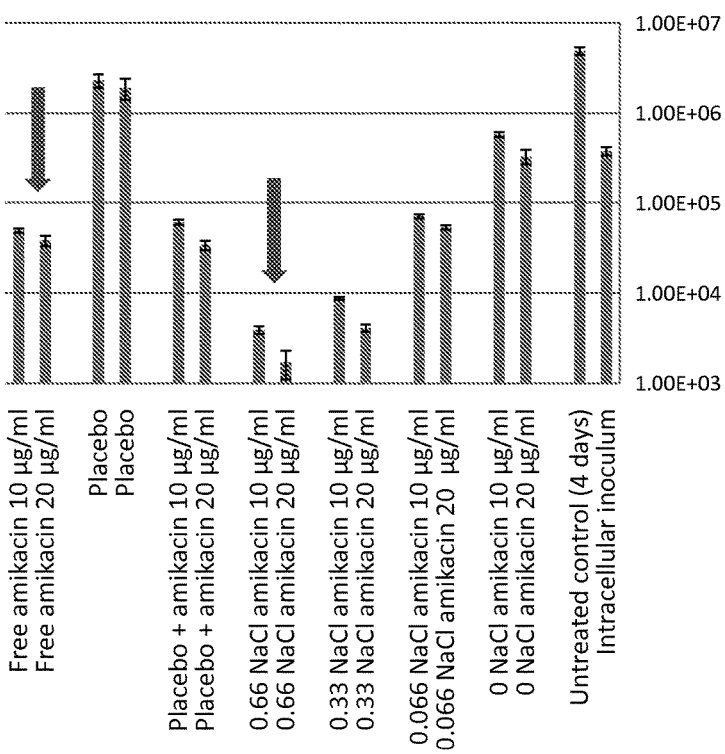
Figure 2:
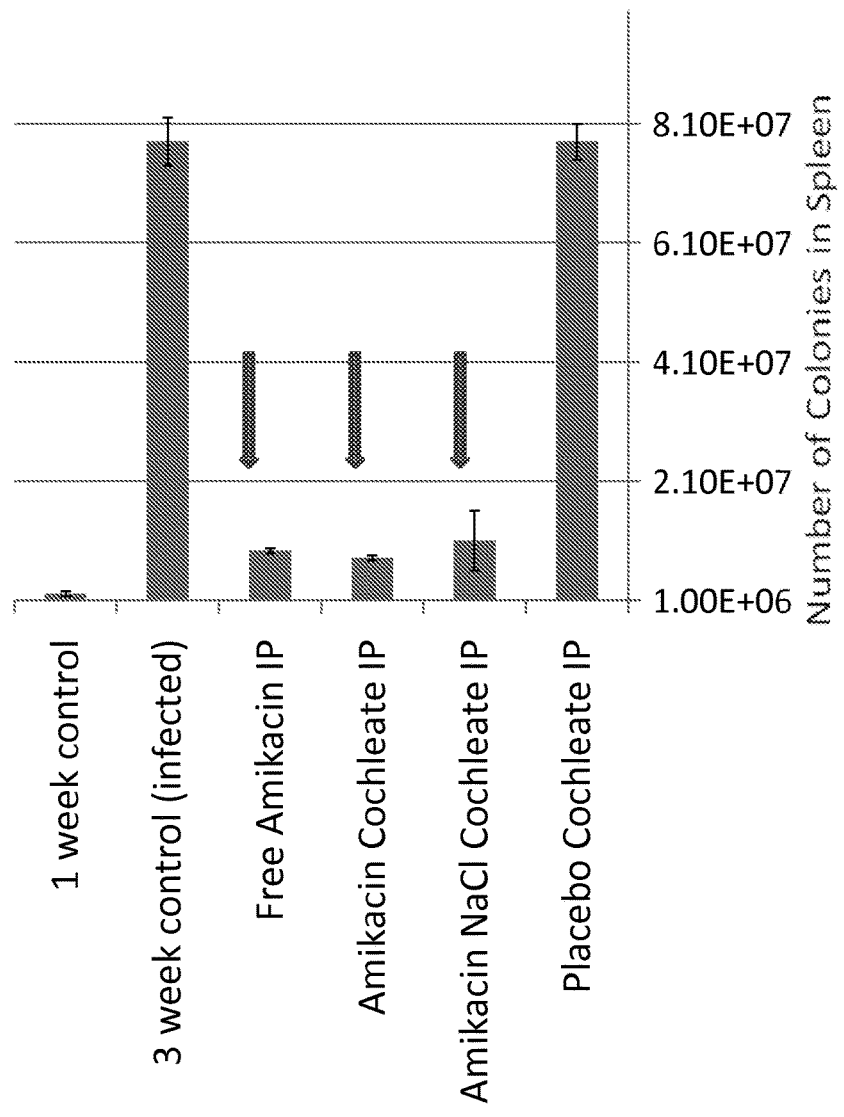
FIG. 2 shows amikacin cochleate in vivo efficacy in a mouse model of MAC 101 infection IP-delivery.
Figure 3:
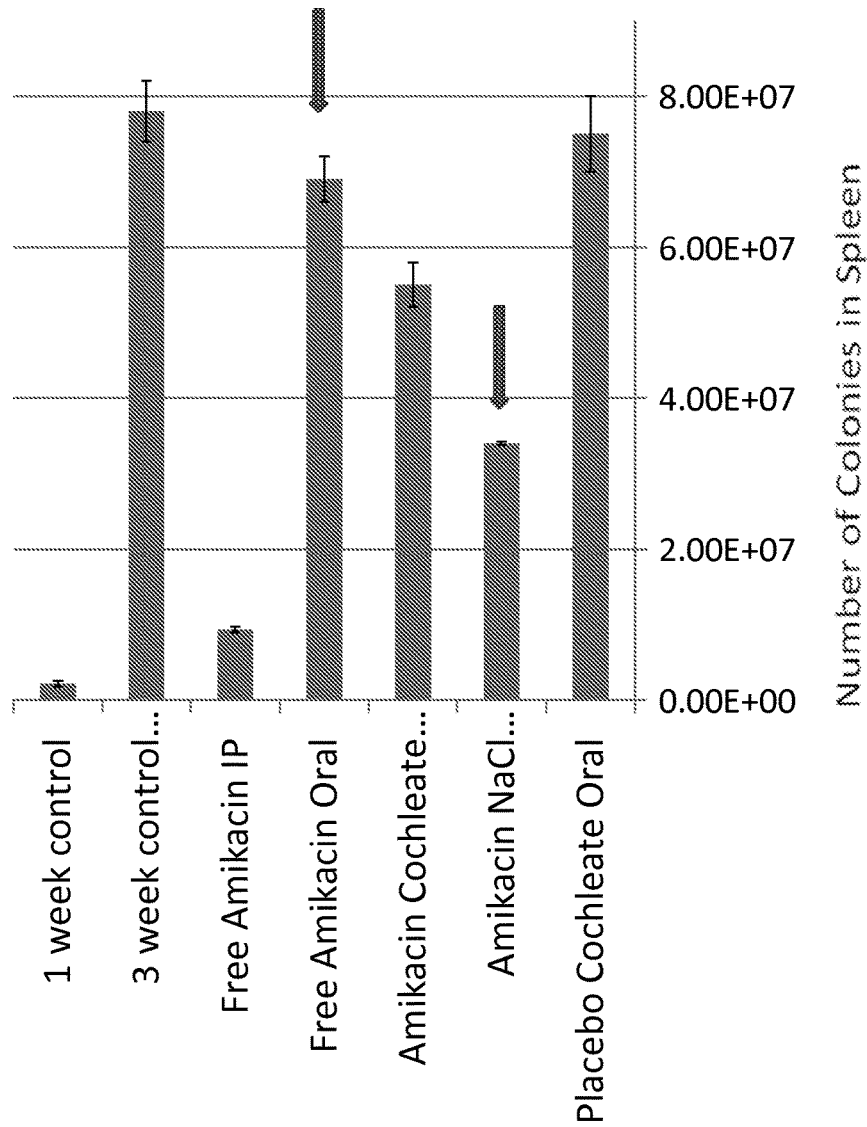
FIG. 3 shows amikacin cochleate in vivo efficacy in a mouse model of MAC 101 infection oral-delivery.

The following terms when used herein will have the definitions given below.

A "cochleate" is a stable, phospholipid-cation precipitate that can be either empty or loaded.

An "empty cochleate" is a cochleate that is comprised only of phospholipid and cations.

A "loaded cochleate" is a cochleate that has one or more biological active compounds within the phospholipid-cation structure.

"Soy phosphatidylserine" or "soy-based phosphatidylserine" is phosphatidylserine that has been derived from a soy based composition.

In practicing the present invention improved phospholipid based cochleates are made by using soy phosphatidylserine in an amount of 40%-74% by weight of the lipid component of the cochleates. Alternatively, the soy phosphatidylserine can be about 40%, 45%, 50%, 55%, 60%, 65%, or 70%, or any incremental value thereof, by weight of the lipid component of the cochleates. It is to be understood that all values, and ranges between these values and ranges are meant to be encompassed by the present invention. In a preferred embodiment the phospholipid comprises 45-70% soy phosphatidylserine. In a more preferred embodiment, the phospholipid comprises 45-55% soy phosphatidylserine.

Phosphatidic acid is a preferred phospholipid that is an additional phospholipid besides phosphatidylserine in the presently improved cochleates. Other phospholipids in addition to phosphatidic acid that can be used in the presently improved cochleates include phosphatidylcholine, phosphatidylinositol and phosphatidylglycerol. Mixtures of the additional phospholipids can also be used in combination with the soy phosphatidylserine.

The soy phosphatidylserine starting material is commercially available, or can be purified from soy phospholipid composition, which are mixtures of several soy phospholipids, according to well known and standard purification techniques.

Any multivalent compound can be used to precipitate the cochleates from the liposome starting materials. Preferably, the multivalent compounds are divalent cations such as $Ca^{++}$, $Zn^{++}$, $Ba^{++}$, and $Mg^{++}$. Preferred sources of these cations include the chloride salts of calcium, zinc, barium, and magnesium. $CaCl_2$ is a particularly preferred source of divalent cations.

In one embodiment, the present soy phosphatidylserine cochleates may further comprise bile salts. The weight ratio of soy-based phospholipid to the bile salts is between 20:1 and 0.5:1, preferably, between 10:1 and 3:1.

Bile salts are bile acids compounded with a cation, usually sodium. Bile acids are steroid acids found predominantly in the bile of mammals. Bile salts are commercially available (for example, Sigma-Aldrich catalog #48305 Fluka cholic acid sodium salt, 50% deoxycholic acid sodium salt, 50%).

It has been unexpectedly found that the addition of bile salts enhances the encochleation efficiency of the soy phosphatidylserine cochleates. For example, with inclusion of bile salts, the soy phosphatidylserine cochleates of the present invention (e.g., with the use of 50% soy PS) are more efficient at encochleating than cochleates containing at least about 75% soy phosphatidylserine.

In one embodiment the present soy phosphatidylserine cochleates are made by a process which comprises the steps of:

a. preparing liposomes in an aqueous medium wherein the liposomes have (i) a lipid bilayer comprising soy-based phosphatidylserine in an amount of about 40%-74% (preferably 45-70%, more preferably 45-55%) by weight of the lipid bilayer and (ii) a load of a biological active;

b. adding a multivalent cation to the suspension of liposomes of (a) to form the soy phosphatidylserine/biological active cochleates; and c. collecting the soy-based phosphatidylserine/biological active cochleates.

In one embodiment, the aqueous medium containing the suspension of liposome is a buffered environment having a pH of 6.5-7.5, and the load of the biological active is at pH 10 or higher prior to addition to the liposomes. In a preferred embodiment, the suspension of liposomes is buffered with phosphate.

In another embodiment, the method further comprises a step of adding bile salts to the suspension of liposomes of (a) before step (b) or adding bile salts to the soy-based phosphatidylserine/biological active cochleates after step (b), wherein the weight ratio of the lipid bilayer to the bile salts is between 20:1 and 0.5:1, preferably, between 10:1 and 3:1.

The present invention provides a geodate composition which contains (1) a lipid monolayer including a soy-based phospholipid that comprises about 40%-74% (preferably 45-70%, more preferably 45-55%) by weight soy phosphatidylserine, disposed about a hydrophobic domain; and (2) a lipid strata disposed about the lipid monolayer, wherein the lipid strata comprises a structure of alternating cationic layers comprising a divalent cation and negatively charged lipid sheet-like layers; and a cargo moiety associated with the hydrophobic domain.

International Patent Application Publication No. WO 2004/041247 has disclosed a process to make a geodate composition, the entire content of which is incorporated herein by reference.

The bioactive active/drug (referred to as "load" or drug) can be hydrophobic in aqueous media, hydrophilic or amphiphilic. The drug can be, but is not limited to, a protein, a small peptide, a bioactive polynucleotide, an antifungal agent, an antiviral agent, an anesthetic, an anti-infectious agent, an antifungal agent, an anticancer agent, an immunosuppressant, a steroidal anti-inflammatory, a nutritional supplement, an herbal product, a vitamin, a non-steroidal anti-inflammatory, a tranquilizer or a vasodilatory agent. Examples include Amphotericin B, acyclovir, adriamycin, vitamin A, cabamazepine, melphalan, nifedipine, indomethacin, naproxen, estrogens, testosterones, steroids, phenytoin, ergotamines, cannabinoids rapamycin, propanidid, propofol, alphadione, echinomycine, miconazole nitrate, teniposide, taxanes, paclitaxel, and taxotere.

The drug can be a polypeptide such as cyclosporin, angiotensin I, II and III, enkephalins and their analogs, ACTH, anti-inflammatory peptides I, II, III, bradykinin, calcitonin, b-endorphin, dinorphin, leucokinin, leutinizing hormone releasing hormone (LHRH), insulin, neurokinins, somatostatin, substance P, thyroid releasing hormone (TRH) and vasopressin.

The drug can be an antigen, but is not limited to a protein antigen. The antigen can also be a carbohydrate or DNA. Examples of antigenic proteins include envelope glycoproteins from influenza or Sendai viruses, animal cell membrane proteins, plant cell membrane proteins, bacterial membrane proteins and parasitic membrane proteins. The antigen is extracted from the source particle, cell, tissue, or organism by known methods. Biological activity of the antigen need not be maintained. However, in some instances (e.g., where a protein has membrane fusion or ligand binding activity or a complex conformation which is recognized by the immune system), it is desirable to maintain the biological activity. In these instances, an extraction buffer containing a detergent which does not destroy the biological activity of the membrane protein is used. Suitable detergents include ionic detergents such as cholate salts, deoxycholate salts and the like or heterogeneous polyoxyethylene detergents such as Tween, BRIG or Triton.

Utilization of this method allows reconstitution of antigens, more specifically proteins, into the liposomes with retention of biological activities, and eventually efficient association with the cochleates. This avoids organic solvents, sonication, or extreme pH, temperature, or pressure all of which may have an adverse effect upon efficient reconstitution of the antigen in a biologically active form.

The presently improved cochleates can include loads with multiple antigenic molecules, biologically relevant molecules or drug formularies as appropriate.

To isolate the cochleate structures and to remove the polymer solution, cochleate precipitates are repeatedly washed with a buffer containing a positively charged molecule, and more preferably, a divalent cation. Addition of a positively charged molecule to the wash buffer ensures that the cochleate structures are maintained throughout the wash step, and that they remain as precipitates.

The medium in which the cochleates are suspended can contain salt such as sodium chloride, sodium sulfate, potassium sulfate, ammonium sulfate, magnesium sulfate, sodium carbonate. The medium can contain polymers such as Tween 80 or BRIG or Triton. The drug-cochleate is made by diluting into an appropriate pharmaceutically acceptable carrier (e.g., a divalent cation-containing buffer).

The cochleate particles can be enteric. The cochleate particles can be placed within gelatin capsules and the capsule can be enteric coated.

The skilled artisan can determine the most efficacious and therapeutic means for effecting treatment practicing the instant invention. Reference can also be made to any of numerous authorities and references including, for example, "Goodman & Gillman's, The Pharmaceutical Basis for Therapeutics", (6$^{th}$ Ed., Goodman et al., eds., MacMillan Publ. Co., New York, 1980).

The improved soy phosphatidylserine cochleates of the present invention containing a biological active are conveniently administered to patients orally whereby the cochleates are absorbed into the bloodstream and the bioactive loads are delivered systemically. This is a particular advantage for water insoluble drugs such as amphotericin-B and paclitaxel. Additionally, the toxicity of many hydrophobic drugs is substantially reduced as seen with soy phosphatidylserine cochleates containing amphotericin-B as the load.

The following examples illustrate the practice of the present invention but should not be construed as limiting its scope.

EXAMPLE 1

Amphotericin B Crystal Cochleate Formulation

Procedures of Amphotericin B Crystal Formulation in Bench Size:

1.1 Experiment Formulation: 43 mg (actually 40 mg Amphotericin B based on the potency assay with the concentration of 0.932 mg/mg) of Amphotericin B in 1.33 mL 0.1N NaOH was mixed with 200 mg dioleoyl phosphatidylserine (DOPS, from Avanti or NOF Corporation) in 6.6 mL 50 mM phosphate buffer pH 7.4 (liposome was filtered through 5 μm filter) to form liposomes containing the Amphotericin B. 29.3 mg calcium chloride was then added into the resultant mixture to form crystal cochleates. To make nice crystalline cochleates, the lipid:Amphotericin B weight ratio was set to about 5:1.

1.2 Experiment Formulation:

18 mg Amphotericin B in 0.6 mL 0.1N NaOH was then mixed with 90 mg DOPS (from Avanti or NOF Corporation) in 3.0 mL 50 mM phosphate buffer pH 7.4 (liposome was filtered through 5 μm, 8 μm, and 4.5 μm filter) to form liposomes containing the Amphotericin B. 0.33 mL 0.5M calcium chloride solution was then added into the resultant mixture to form crystals Amphotericin B cochleates. To make nice crystalline cochleates, the lipid:Amphotericin B weight ratio was about 5:1.

Procedures of Amphotericin B (Amphotericin B) Crystals Cochleates in Small Scale Size:

1.3 Experiment Formulation:

399 mg (actually 372 mg based on the potency assay with the concentration of 0.932 mg/mg) Amphotericin B in 12.4 mL 0.1N NaOH solution was combined with 1.86 g of 50% soy PS (American Lecithin Company or Lipoid LLC) in 62 mL 50 mM phosphate buffer pH 7.4 (liposome was filtered through 5 μm filter) to form liposomes containing the Amphotericin B. In order to add an antioxidant the suspension, 372 mg vitamin E in 3.72 mL ethyl alcohol was then added into the mixture of the liposomes. 520 mg powder of calcium chloride was then added into the resultant mixture to form Amphotericin B crystals cochleates. To make nice crystalline cochleates of Amphotericin B, the lipid:Amphotericin B weight ratio was about 5:1.

Procedures of Amphotericin B Crystal Formulation Scale up to 4.5 L:

1.4 Experiment Formulation:

22.75 g Amphotericin B (actually 21.2 g Amphotericin B based on the potency assay with the concentration of 0.932 mg/mg) in 707 mL 0.1N NaOH solution was then mixed with 106 g of 50% soy PS in 3.533 L 50 mM phosphate buffer pH 7.4 (liposome was filtered through 10 μm filter) to form liposomes containing the Amphotericin B. To make a stable suspension of cochleates, 372 mg vitamin E in 3.72 mL ethyl alcohol was then added into the mixture. 194.8 mL 1M calcium chloride was then added into the resultant mixture to form crystal cochleates. The final product of cochleates was lyophilized with Freezer Dryer for a few days. To make nice crystalline cochleates of Amphotericin B, the lipid:drug weight ratio was set to about 5:1.

EXAMPLE 2

Curcumin (Granular) Geode Cochleates Formulation

Procedures of Curcumin (granular) Geode Cochleates in Small Scale Size:

2.1 Experiment Formulation:

50 mg curcumin in 1 g castor oil and 4.0 mL ethyl alcohol was dissolved first then combined with 19 of 75% soy PS (American Lecithin Company or Lipoid LLC) in 100 mL sterile water (liposome was filtered through Sum filter) to form liposomes containing the curcumin. In order to decrease the stickiness of suspension and batter diffusion, 500 mg bovine serum albumin ("BSA", or casein) was then added into the mixture of the liposome. 16.9 mL 0.1M calcium chloride was then added into the resultant mixture to form curcumin geode cochleates. The final product of goede cochleates was lyophilized with a freezer dryer for a few days. To make nice geode cochleates of curcumin, the lipid:drug weight ratio was set to about 20:1.

2.2 Experiment Formulation:

1.00 mg 75% soy PS in 100 mg sterile water (liposome was filtered through Sum filter) was mixed with 500 mg casein (or BSA) and then mixed with 50 mg curcumin in 2.0 g castor oil and 4.0 mL ethyl alcohol to form liposome containing the curcumin: 16.9 mL 0.1M calcium chloride was then added into the resultant mixture to form geode cochleates. The final product of goede cochleates was lyophilized with a freezer dryer for a few days. To make nice geode cochleates of curcumin, the lipid:drug weight ratio was set to about 20:1.

Procedures of Curcumin (Granular) Crystal Formulation in Small Scale Size:

2.3 Experiment Formulation:

1000 mg 75% soy PS in 100 mL sterile water was (liposome was filtered through Sum filter) combined with 20 mg curcumin in 4.0 mL ethyl alcohol to form liposome containing the curcumin. In order to help the drug stable in the lipid bilayer, 500 mg casein (or BSA) was then added into the suspension of the liposome. 16.9 mL 0.1M calcium chloride was then added into the resultant mixture to form crystal cochleates. The final product of crystal cochleates was lyophilized with Freezer Dryer for a few days. To make nice crystalline cochleates, the lipid:curcumin weight ratio was set to about 50:1.

2.4 Experiment Formulation:

1000 mg 75% soy PS in 100 mL, sterile water was (liposome was filtered through 5 μm filter) combined with 20 mg curcumin in 4.0 mL, ethyl alcohol to form liposome containing the curcumin. 16.9 mL 0.1M calcium chloride was then added into the resultant mixture to form crystal cochleates. In order to help the drug stable in the lipid bilayer, 500 mg casein (or BSA) was then added into the suspension of the cochleates. The final product of crystal cochleates was lyophilized with a Freezer Dryer for a few days. To make nice crystalline cochleates, the lipid:curcumin weight ratio was set to about 50:1.

EXAMPLE 3

Amphotericin B (Amphotericin B) Geode Formulation

Procedures of Amphotericin B (Amphotericin B) Geode Formulation in bench Size:

3.1 Experiment Formulation:

7.5 mg Amphotericin B (actually 7 mg based on the potency assay with the concentration of 0.932 mg/mg) In 0.2 mL 0.1N NaOH solution was mixed with 50 mg of castor oil and then combined with 35 mg of 50% soy PS in 1.75 mL sterile water (liposome was filtered through 5 μm filter) to form geode liposomes containing the Amphotericin B. To prevent the stickiness of Amphotericin B geode formulation, 21 mg BSA or casein was then added into the mixture of the Amphotericin B geode liposome. To increase the stability of the Amphotericin B geode formulation, 7 mg vitamin E in 70 μL Ethyl alcohol was then added into the mixture of the geode liposome. To the resultant mixture, 127 μL of 0.5M calcium chloride was then added to form Amphotericin B geode cochleates. To make a nice geode cochleates of Amphotericin B, the lipid:Amphotericin B weight ratio was about 5:1.

Procedures of Amphotericin B Geode Formulation Scale Up to 150 mL:

3.2 Experiment Formulation:

536 mg Amphotericin B (actually 500 mg based on the potency assay with the concentration of 0.932 mg/mg) In 14.3 mL 0.1N NaOH solution was then mixed with 3.57 g castor oil and then combined with 2.5 g of 50% soy PS in 125 mL sterile water (liposome was filtered through 5 μm filter) to form geode liposomes containing the Amphotericin B. To prevent the stickiness of the geode formulation, 1.5 g BSA or casein was then added into the mixture of geode liposome. To increase the stability of the Amphotericin B geode formulation, 250 mg of vitamin E in 2.5 mL ethyl alcohol was then added into the mixture of the geode liposome. To the resultant mixture was then added 8.88 mL of 0.5M calcium chloride to form geode cochleates. The pH of the final mixture was adjusted to neutral with 0.3 mL 1N HCl. To make nice geode cochleates of Amphotericin B, the lipid:Amphotericin B weight ratio was about 5:1.

3.3 Experiment Formulation:

2.5 g of 50% soy PS in 125 mL sterile water (liposome was filtered through 5 μm filter) was mixed with 1.5 g of BSA or casein and then combined with 536 mg of Amphotericin B (actually 500 mg based on the potency assay with the concentration of 0.932 mg/mg) in 14.3 mL 0.1N NaOH solution with 3.57 g of castor oil to form liposomes containing the Amphotericin B. To make a stable geode formulation, 250 mg vitamin E in 2.5 mL ethyl alcohol was then added into the mixture of geode liposome. The pH of the final mixture was adjusted to neutral with 0.3 mL 1N HCl. 8.88 mL of 0.5M calcium chloride was then added to the resultant mixture to form geode cochleates. Geode cochleates were then concentrated using lyophilization to provide geode cochleates with sterile water in any concentrations (based on the experiment requirements) with a lipid:Amphotericin B weight ratio of about 5:1.

EXAMPLE 4

Amikacin Crystal Cochleate Formulation for In Vitro Study

Procedure of Amikacin Formulation for In Vitro Study:

4.1 Experiment Formulation:

2 mg amikacin in 1.0 mL distilled deionized (D.D) water was filtered through 0.22 μm filter and combined with 20 mg of 50% soy PS in 2.0 mL sterile water (liposome was filtered through 5, 0.8 and 0.45 μm filter) to form liposomes containing the amikacin. To the resultant mixture was then added 0.206 mL of 0.1M calcium chloride to form cochleates. The mixture was then adjusting the drug concentration of the amikacin at 0.5 mg/mL with sterile water. To make nice crystalline cochleates of amikacin with a lipid:drug ratio of about 10:1.

4.2 Experiment Formulation:

2 mg amikacin in 1.0 mL D.D water was filtered through 0.22 μm filter and combined with 20 mg of 50% soy PS in 2.0 mL sterile water (liposome was filtered through 5, 0.8 and 0.45 μm filter) to form liposomes containing the amikacin. To the resultant mixture was then added 0.206 mL of 0.1M calcium chloride to form cochleates. To reduce the aggregation size of the crystals cochleates, 15 mg sodium chloride in 52 μl sterile water was then added to the mixture of the cochleates. The mixture was then adjusting the concentration of the amikacin at 0.5 mg/mL with sterile water. Also, the final product containing the 0.066M sodium chloride. To make nice crystalline cochleates of amikacin with a lipid:drug ratio of about 10:1.

4.3 Experiment Formulation:

2 mg amikacin in 1.0 mL D.D water was filtered through 0.22 μm filter and combined with 20 mg of 50% soy PS in 2.0 mL sterile water (liposome was filtered through 5, 0.8 and 0.45 μm filter) to form liposomes containing the amikacin. To the resultant mixture was then added 0.206 mL of 0.1M calcium chloride to form cochleates. To reduce the aggregation size of the crystals cochleates, 76 mg sodium chloride in 264 μl sterile water was then added to the mixture of the cochleates. The mixture was then adjusting the concentration of the amikacin at 0.5 mg/mL with sterile water. Also, the final product containing 0.33M sodium chloride. To make nice crystalline cochleates of amikacin with a lipid:drug ratio of about 10:1.

4.4 Experiment Formulation:

2 mg amikacin in 1.0 mL D.D water was filtered through 0.22 μm filter and combined with 20 mg of 50% soy PS in 2.0 mL sterile water (liposome was filtered through 5, 0.8 and 0.45 μm filter) to form liposomes containing the amikacin. To the resultant mixture was then added 0.206 mL of 0.1 M calcium chloride to form cochleates. To reduce the aggregation size of the crystals cochleates, 152 mg sodium chloride in 524 μl sterile water was then added to the mixture of the cochleates. The mixture was then adjusting the concentration of the amikacin at 0.5 mg/mL with sterile water. Also, the final product containing 0.66M sodium chloride. To make nice crystalline cochleates of amikacin with a lipid:drug ratio of about 10:1.

EXAMPLE 5

Amikacin Crystal Cochleate Formulation for In Vivo Study

Procedure of Amikacin Formulation for In Vivo Study:

5.1 Experiment Formulation:

200 mg amikacin in 20 mL D.D water was filtered through 0.22 μm filter and combined with 2000 mg of 50% soy PS in 200 mL sterile water (liposome was filtered through 5, 0.8 and 0.45 μm filter) to form liposomes containing the amikacin. To the resultant mixture was then added 17 mL of 0.1M calcium chloride to form cochleates. Cochleates were then concentrated under lyophilization to provide crystal cochleates (about 6.7 mg/mL) with a lipid:amikacin ratio of about 10:1.

5.2 Experiment Formulation:

200 mg amikacin in 20 mL D.D water was filtered through 0.22 μm filter and combined with 2000 mg of 50% soy PS in 200 mL sterile water (liposome was filtered through 5, 0.8 and 0.45 μm filter) to form liposomes containing the amikacin. To the resultant mixture was then added 17 mL of 0.1M calcium chloride to form cochleates. To reduce the aggregation size of crystals cochleates, 1125.2 mg sodium chloride in 3.88 mL sterile water was then added to the mixture of the cochleates. Cochleates were then concentrated under lyophilization to provide crystal cochleates (about 6.7 mg/mL and 0.66M sodium chloride) with a lipid:amikacin ratio of about 10:1.

EXAMPLE 6

In Vitro Study of Aminoglycosides Crystal Cochleate Formulation

Macrophages and Infection

Cell lines: mouse peritoneal macrophage cell line (Raw 246.7), and/or THP-1, a human macrophage cell line. Cells were cultured in DMEM and RPMI-1640, respectively, supplemented with 5% heat-inactivated fetal bovine serum. Macrophage monolayers were established by adding $10^5$ macrophages to a 24-well tissue culture plate. After 24 hours, monolayers were infected and the infection was allowed to happen for 1 hour, and then the extracellular bacteria were removed by washing. Some of the well contents were lysed and plated onto Middlebrook 7H10 agar plate, to determine the intracellular inoculum of the bacterium. The remaining wells were treated daily with different aminoglycosides (i.e., amikacin, gentamicin, and paromomycin) cochleates prepared in accordance with the claimed method. After treatment, cell monolayers were lysed and the lysate plated into 7H10 agar to quantify the intracellular load.

TABLE 1

Efficacy Comparison between Encochleated Aminoglycosides Formulation and Free Aminoglycosides

| Results | Enhanced Efficacy vs. Free Drug |
|---|---|
| Amikacin | *Mycobacterium avium* (10x-20x) |
| | *Mycobacterium* tuberculosis (7x) |
| | *Francisella tularensis* LVS (3x) |
| Gentamicin | *Mycobacterium avium* (10x) |
| | *Mycobacterium* smegmatis (50x) |
| | *Mycobacterium* tuberculosis (2x) |
| | *Francisella tularensis* LVS (2x) |
| | *Francisella tularensis* type A (4x) |
| Paromomycin | *Francisella tularensis* type A (4x) |
| | Cutaneous Leishmaniasis (3x) |

As indicated in Table 1, aminoglycoside cochleates have enhanced efficacy against different bacteria compared to corresponding non-encochleated free drugs.

EXAMPLE 7

In Vitro Study of Amikacin Crystal Cochleate Formulation

Methods: As shown in Example 4, amikacin cochleate (Amkcch) formulations were optimized for amikacin encochleation efficiency and particle size by varying the type of PS used, the PS:biological active ratio, PS:$Ca^{++}$ ratio, and NaCl concentration. The efficacy of Amkcch against intracellular Ma infections was evaluated in vitro using mouse peritoneal macrophage infected with *M. avium* strains MAC 101 or MAC 109. Mouse peritoneal macrophages (Mo) Raw 264.7 cells were seeded at 105 cells/well. Mo monolayers were infected at ratio 1:10 for 1 h and extracellular bacteria removed. Monolayers were treated with free amikacin and/or cochleate preparations for 4 days and the number of intracellular bacteria determined. Assays were repeated three times.

Results: Untreated control Ma strains grew within Mo from 3.8' 105 to 4.9' 106. Ma within Mo treated with free amikacin (10 and 20 mg/mL) were killed to 6.1 and 3.4' 104 bacteria, respectively. Optimized Amkcch (10 and 20 mg/mL) demonstrated greater than 10-fold enhanced efficacy, reducing bacterial count to 3.9 and 1.7' 103 bacteria within Mo (p<0.05 compared with free amikacin).

Conclusions: As indicated in the FIG. 1, amikacin cochleate formulations are 10-50 fold more active than free amikacin against *M. avium* infection in macrophage. Cochleate preparations of amikacin showed significant and enhanced activity against Ma strains in macrophages, suggesting that cochleates achieved higher intracellular concentration for a longer time than free amikacin.

EXAMPLE 8

In Vivo Study of Amikacin Crystal Cochleate Formulation

A formation of amikacin cochleates has been developed. The in vivo efficacy amikacin cochleates against Mycobacterium avium complex (MAC) was evaluated using C57BL/6 black mice.

Mice, 12/group, were infected with *M. avium* 101 (8.1×107 bacterial/mouse) by tail vein injection.

After 7 days, 6 mice were harvested an the number of MAC in spleen was quantified to establish the baseline bacterial load (Time 0).

Mice were treated with various amikacin cochleates as indicated in FIGS. 2 and 3 at 1.0 mg amikacin/day for 2 weeks.

Mice were harvested at week 3 and 2 days later (after 2 weeks of treatment), and spleens homogenized and plated onto 7H10 agar.

Colonies on plates were counted and the data were analyzed.

As demonstrated in FIGS. 2 and 3, amikacin cochleates, given I.P. or orally, were active, reducing the number of bacterial load in the spleen. The amikacin cochleate preparation with high salt concentration does orally was Conclusion: Oral delivery of Amikacin cochleate formulations demonstrates in vivo efficacy similar to IP free amikacin.

EXAMPLE 9

High Salt Procedure for Aminoglycoside Formulations for In Vitro Study

9.1 Experiment Formulation:

2 mg aminoglycoside in 1.0 ml D.D water was filtered through 0.22 μm filter and combined with 20 mg of 50% soy PS in 2.0 ml sterile water (liposome was filtered through 5, 0.8 and 0.45 μm filter) to form liposomes containing the aminoglycoside. To the resultant mixture was then added 0.206 ml of 0.1M calcium chloride to form cochleates. The mixture was then adjusting the drug concentration of the aminoglycoside at 0.5 mg/ml with sterile water. To make nice crystalline cochleates of aminoglycoside with a lipid:drug ratio of about 10:1.

9.2 Experiment Formulation:

2 mg aminoglycoside in 1.0 ml D.D water was filtered through 0.22 μm filter and combined with 20 mg of 50% soy PS in 2.0 ml sterile water (liposome was filtered through 5, 0.8 and 0.45 μm filter) to form liposomes containing the aminoglycoside. To the resultant mixture was then added 0.206 ml of 0.1M calcium chloride to form cochleates. To reduce the aggregation size of the crystals cochleates, 76 mg sodium chloride in 264 μl sterile water was then added to the mixture of the cochleates. The mixture was then adjusting the concentration of the aminoglycoside at 0.5 mg/ml with sterile water. Also, the final product containing the 0.066M sodium chloride. To make nice crystalline cochleates of aminoglycoside with a lipid:drug ratio of about 10:1.

9.3 Experiment Formulation:

2 mg aminoglycoside in 1.0 ml D.D water was filtered through 0.22 μm filter and combined with 20 mg of 50% soy PS in 2.0 ml sterile water (liposome was filtered through 5, 0.8 and 0.45 μm filter) to form liposomes containing the aminoglycoside. To the resultant mixture was then added 0.206 ml of 0.1M calcium chloride to form cochleates. To reduce the aggregation size of the crystals cochleates, 152 mg sodium chloride in 524 μl sterile water was then added to the mixture of the cochleates. The mixture was then adjusting the concentration of the aminoglycoside at 0.5 mg/ml with sterile water. Also, the final product containing 0.33M sodium chloride. To make nice crystalline cochleates of aminoglycoside with a lipid:drug ratio of about 10:1.

9.4 Experiment Formulation:

2 mg aminoglycoside in 1.0 ml D.D water was filtered through 0.22 μm filter and combined with 20 mg of 50% soy PS in 2.0 ml sterile water (liposome was filtered through 5, 0.8 and 0.45 μm filter) to form liposomes containing the aminoglycoside. To the resultant mixture was then added 0.206 ml of 0.1M calcium chloride to form cochleates. To reduce the aggregation size of the crystals cochleates, 152 mg sodium chloride in 524 μl sterile water was then added to the mixture of the cochleates. The mixture was then adjusting the concentration of the aminoglycoside at 0.5 mg/ml with sterile water. Also, the final product containing 0.66M sodium chloride. To make nice crystalline cochleates of aminoglycoside with a lipid:drug ratio of about 10:1.

TABLE 2

Results of Amikacin Encochleation for in House Study Obtained from Amikacin-cochleation Supernatant (Degussa 85% vs Lipoid 50% Soy PS and before and after lyophilization)

| Measured by using | Ratio of the Lipid:Drug | Deguss 85% bSoy PS before lyophilization | Deguss 85% bSoy PS After lyophilization | Lipoid 50% Soy PS before lyophilization | Lipoid 50% Soy PS After lyophilization |
|---|---|---|---|---|---|
| Buffer | 20:1 | 34% in sup | 39.5% in sup | 34.5% in sup | 33.8% in sup |
| Buffer | 10:1 | 69.1% in sup | 72.6% in sup | 50% in sup | 48.3% in sup |
| Buffer | 5:1 | 74.7% in sup | 83.5% in sup | 61.3% in sup | 58.1% in sup |

TABLE 2-continued

Results of Amikacin Encochleation for in House Study Obtained from Amikacin-cochleation
Supernatant (Degussa 85% vs Lipoid 50% Soy PS and before and after lyophilization)

| Measured by using | Ratio of the Lipid:Drug | Deguss 85% bSoy PS before lyophilization | Deguss 85% bSoy PS After lyophilization | Lipoid 50% Soy PS before lyophilization | Lipoid 50% Soy PS After lyophilization |
|---|---|---|---|---|---|
| Degussa 85% soy PS Plain Sup | 20:1 | 25.3% in sup | 30.2% in sup | 25.7% in sup | 25% in sup |
| Degussa 85% soy PS Plain Sup | 10:1 | 55.4% in sup | 58.4% in sup | 38.4% in sup | 36.8% in sup |
| Degussa 85% soy PS Plain Sup | 5:1 | 61.6% in sup | 69.5% in sup | 49.5% in sup | 47% in sup |
| Lipoid 50% Soy PS Plain Sup | 20:1 | 29.6% in sup | 34.3% in sup | 30% in sup | 29.5% in sup |
| Lipoid 50% Soy PS Plain Sup | 10:1 | 59.8% in sup | 62.9% in sup | 43.6% in sup | 42.4% in sup |
| Lipoid 50% Soy PS Plain Sup | 5:1 | 64.3% in sup | 72.2% in sup | 52.8% in sup | 50.8% in sup |

Encochleation percentage is determined by measuring the amount of amikacin in the supernatant (ninhydrin assay) after forming the cochleates and then centrifuging. The amount in the supernatant is then subtracted from the total amount during the encochleation process. This is reported as percent in supt. The lower the percent in supernatant the higher the encochleation efficiency. The results listed in Table 2 clearly demonstrate that 50% soy PS is more efficient at encochleating than 85% PS.

TABLE 3

Results of Amikacin Formulation Obtained from Absorbance at 400 nm

| Measured by Using | Ratio of 50% soy PS to drug (10:1) | Ratio of 85% soy PS to drug (10:1) | Ratio of 50% soy PS to drug (20:1) | Ratio of 85% soy PS to drug (20:1) | Ratio of 50% soy PS to drug (5:1) | Ratio of 85% soy PS to drug (5:1) |
|---|---|---|---|---|---|---|
| 50 mM Phosphate buffer + Amikacin | 50.6% in sup | 94.4% in sup | 34.8% in sup | 54.9% in sup | 53.5% in sup | 76.4% in sup |
| 50% soyPS Plain sup + Amikacin | 41% in sup | 79% in sup | 27.9% in sup | 45.2% in sup | 44.3% in sup | 63.8% in sup |
| 85% soyPS Plain sup + Amikacin | 44% in sup | 82.8% in sup | 30% in sup | 47.8% in sup | 46.8% in sup | 66.9% in sup |

Encochleation percentage is determined by measuring the amount of amikacin in the supernatant (ninhydrin assay) after forming the cochleates and then centrifuging. The amount in the supernatant is then subtracted from the total amount during the encochleation process. This is reported as percent in supt. The lower the percent in supernatant the higher the encochleation efficiency. The results listed in Table 3 clearly demonstrate that 50% soy PS is more efficient at encochleating than 85% PS.

TABLE 4

Results of Amikacin Formulation Obtained from Absorbance at 400 nm

| Measured by Using | Ratio of DOPS to Amikacin | Lipoid 50% Soy PS | Avanti DOPS | Avanti 99% Soy PS | NOF DOPS |
|---|---|---|---|---|---|
| 50 mM Phosphate buffer | 10:1 | 47.3% in sup | 87.7% in sup | 84.3% in sup | 86.4% in sup |
| Lipoid 50% soy PS Plain cochleates sup | 10:1 | 37.1% in sup | 77% in sup | 73.5% in sup | 64% in sup |
| Avanti DOPS plain sup | 10:1 | 43.6% in sup | 83% in sup | 80% in sup | 81.7% in sup |
| Avanti 99% soy PS plain sup | 10:1 | 41.9% in sup | 84.6% in sup | 81% in sup | 83% in sup |

Encochleation percentage is determined by measuring the amount of amikacin in the supernatant (ninhydrin assay) after forming the cochleates and then centrifuging. The amount in the supernatant is then subtracted from the total amount during the encochleation process. This is reported as percent in supt. The lower the percent in supernatant the higher the encochleation efficiency. The results listed in Table 4 clearly demonstrate that 50% soy PS is more efficient at encochleating than 99.99% PS.

Figure 4:
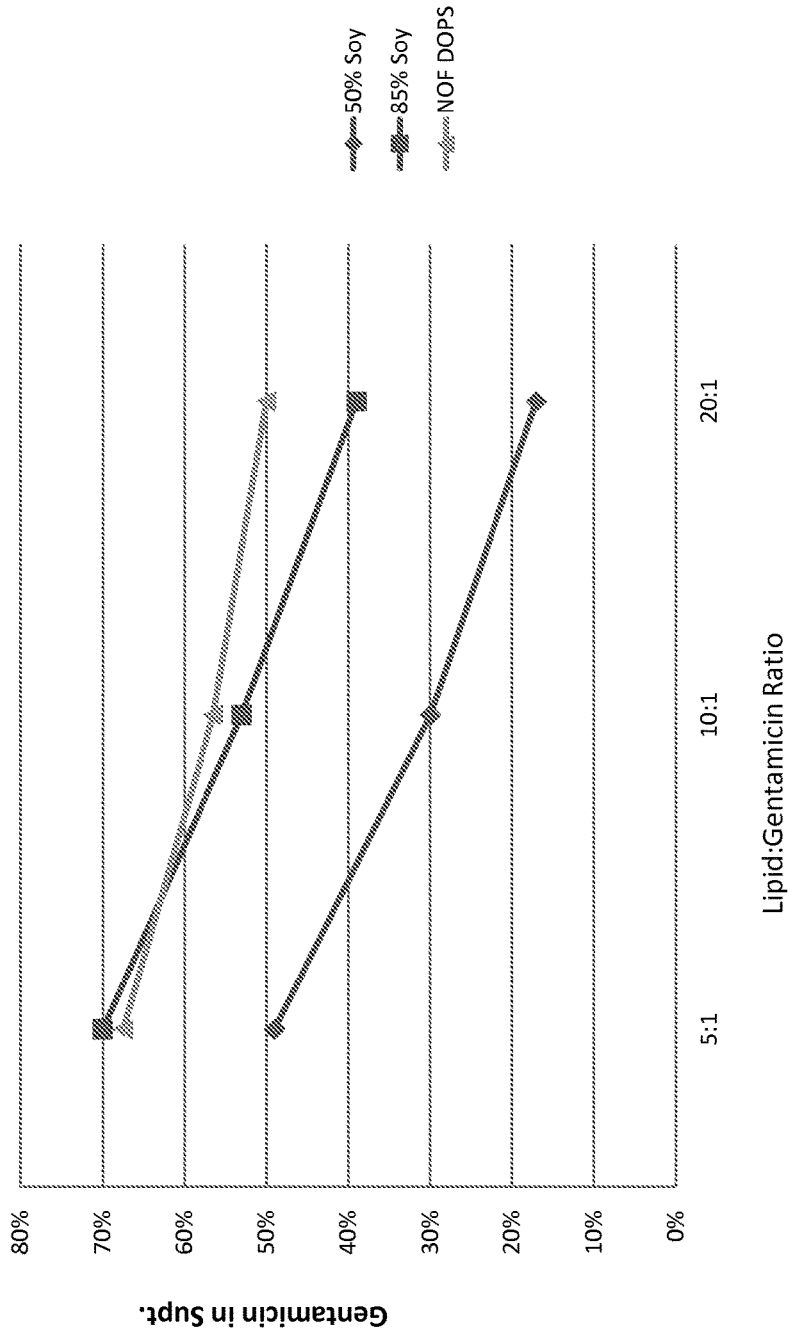
FIG. 4 shows gentamicin encochleation related to PS properties.
Figure 5:
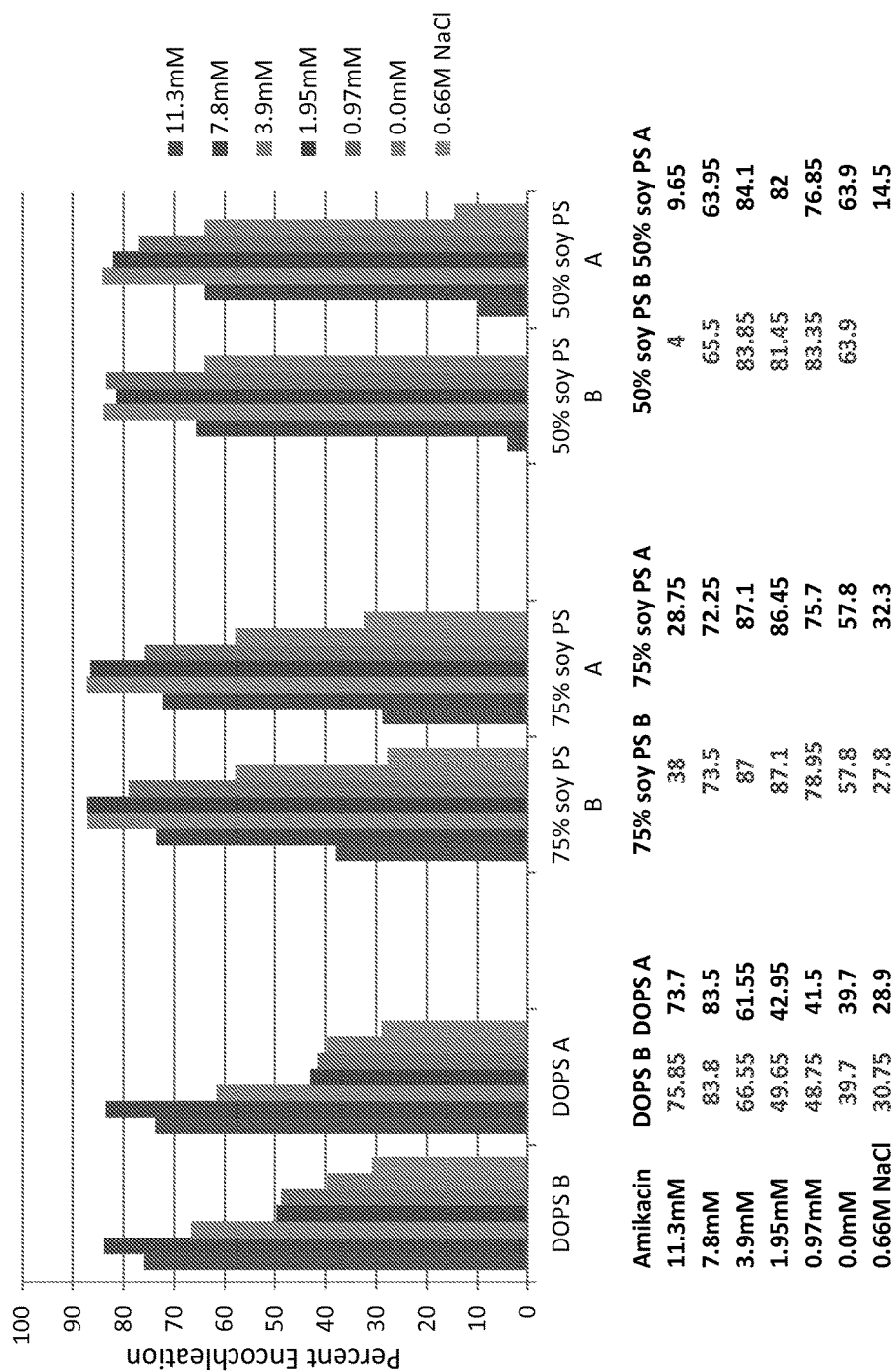
FIG. 5 shows encochleation efficiency of amikacin bile salts related to PS properties.
Figure 6:
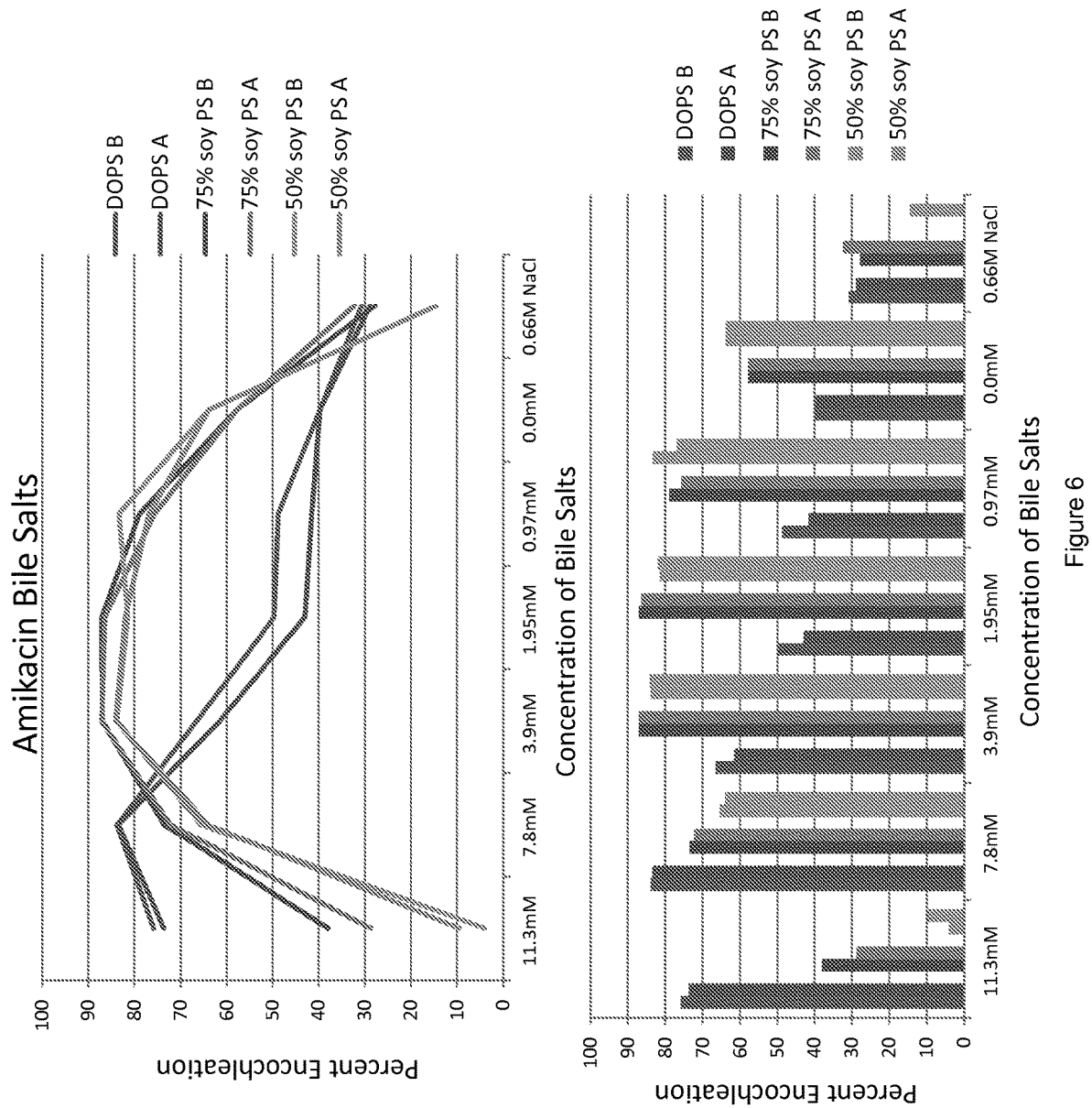
FIG. 6 shows encochleation efficiency of amikacin bile salts related to PS properties.
Figure 7:
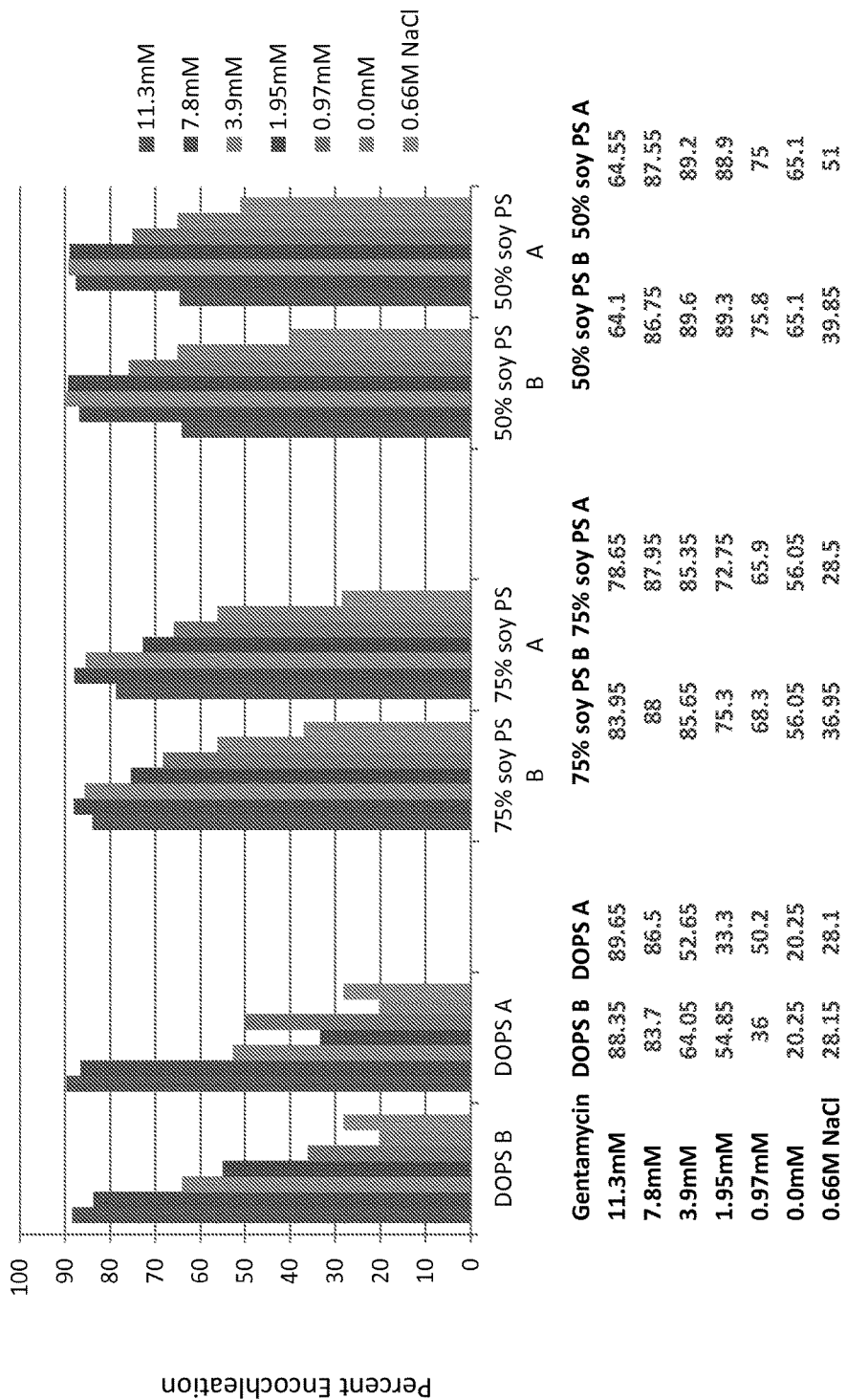
FIG. 7 shows encochleation efficiency of gentamycin bile salts related to PS properties.
Figure 8:
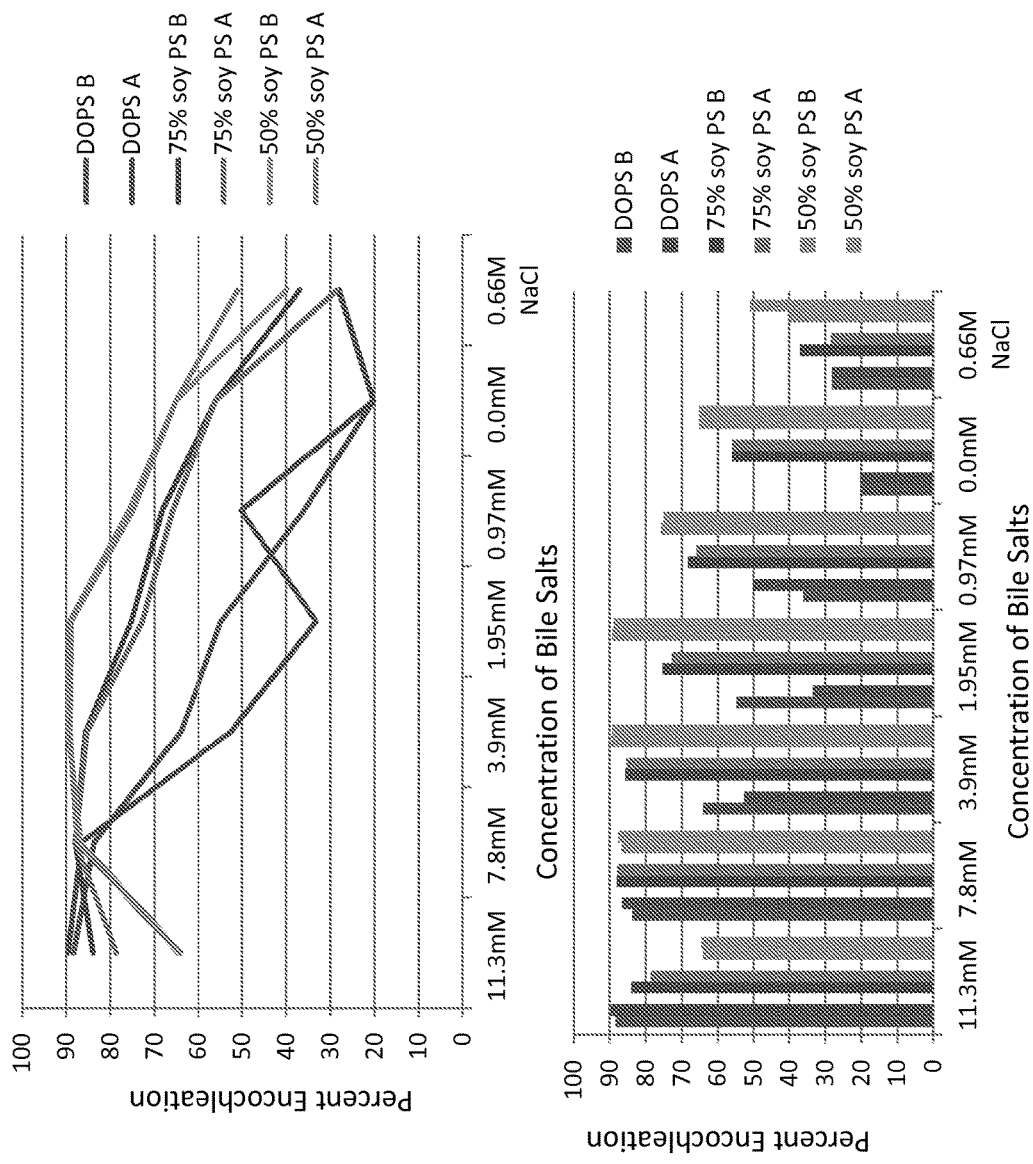
FIG. 8 shows encochleation efficiency of gentamycin bile salts related to PS properties.
Figure 9:
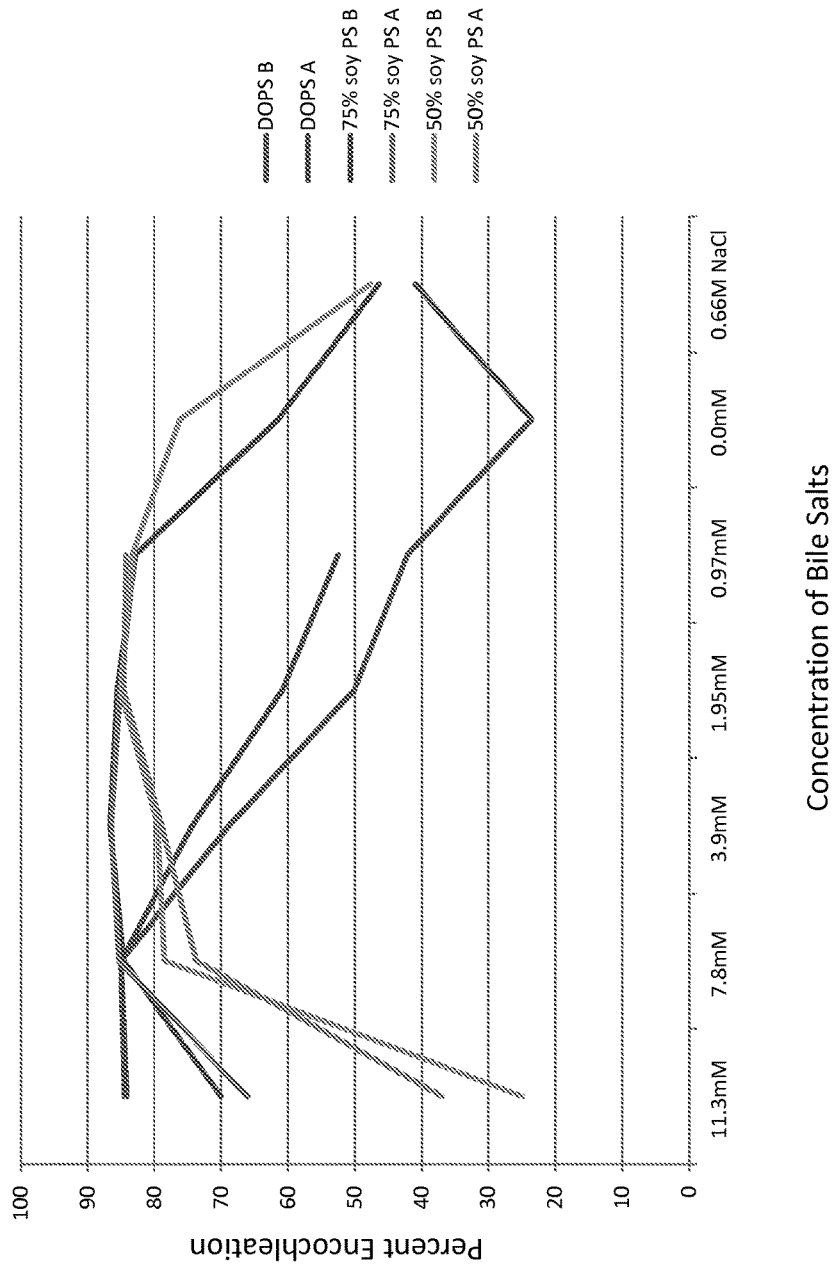
FIG. 9 shows encochleation efficiency of paromomycin bile salts related to PS properties.
Figure 10:
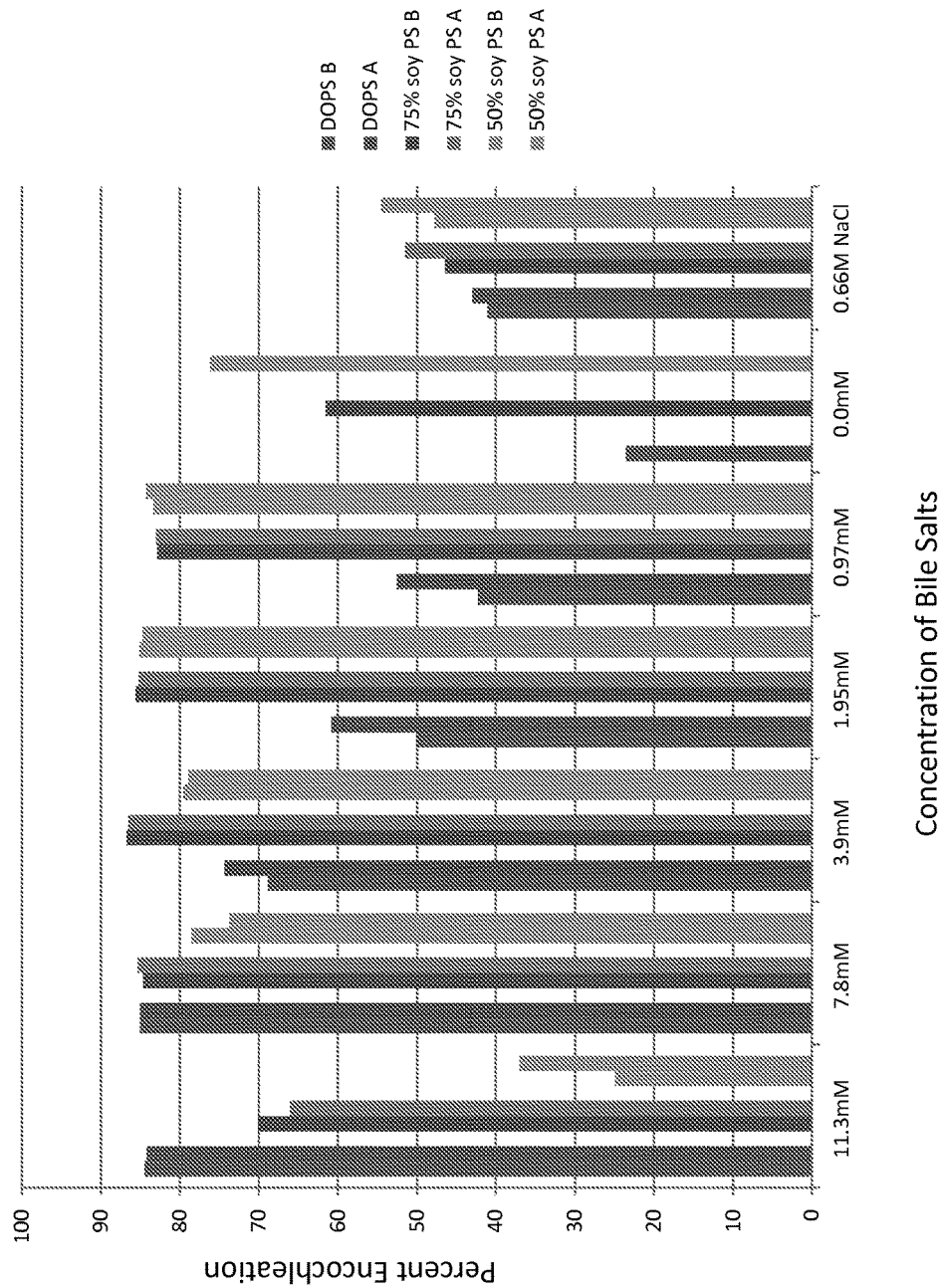
FIG. 10 shows encochleation efficiency of paromomycin bile salts related to PS properties.
Figure 11:
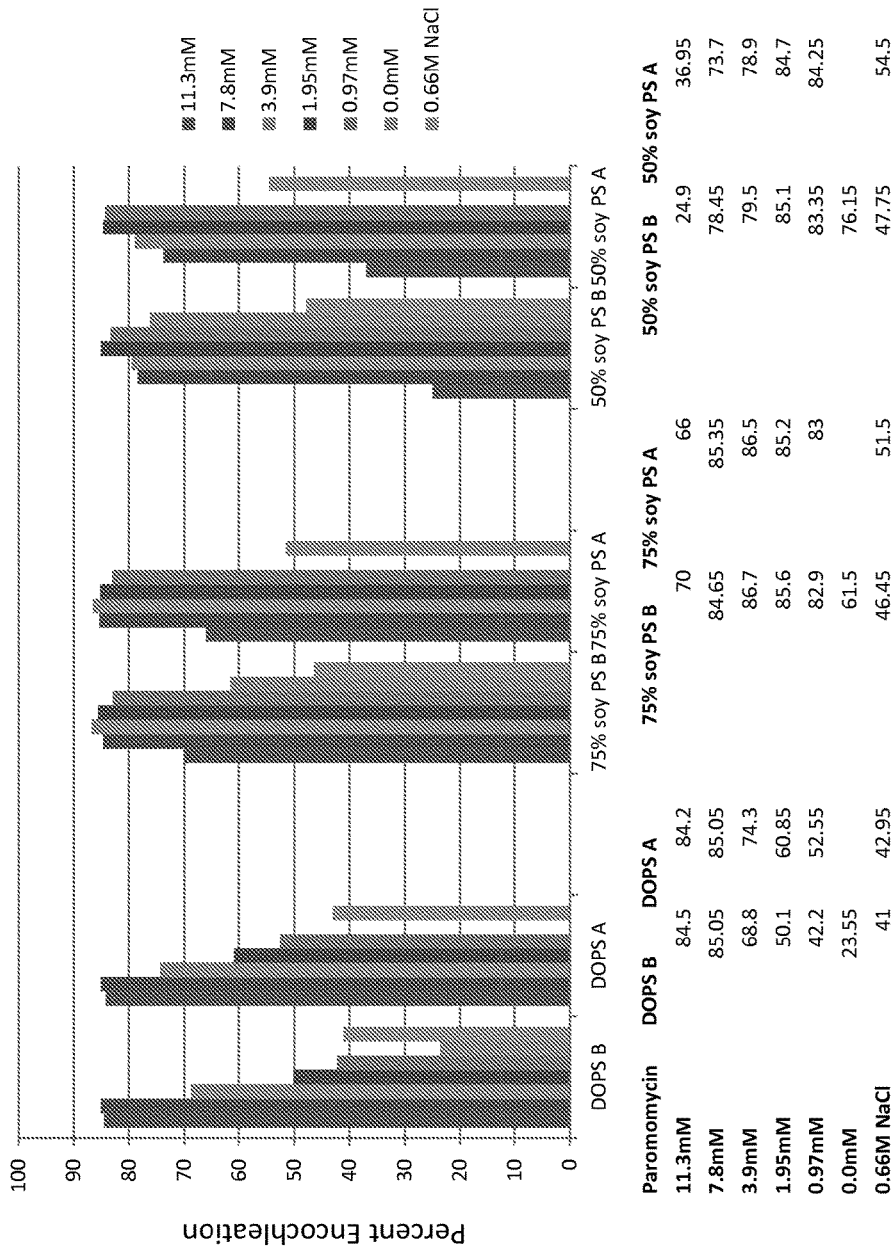
FIG. 11 shows encochleation efficiency of paromomycin bile salts related to PS properties.

FIG. 4 shows Gentamicin Encochleation Related to PS Properties. Similar to Tables 1-3, the results listed in FIG. 4 clearly demonstrate that 50% soy PS is more efficient at encochleating gentamicin at lower bile salt concentrations than 85% PS or 99.99% PS.

EXAMPLE 10

Encochleation Efficiency of Amikacin, Gentamicin, and Paromomycin Bile Salt Cochleates

10.1 Procedure for Aminoglycoside Formulation with Bile Salts (after Calcium) for In Vitro Studies.

Crystalline cochleates of aminoglycoside formulation with different amount of bile salts (Sigma-Aldrich catalog #48305 Fluka cholic acid sodium salt, 50% deoxycholic acid sodium salt, 50%):

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. To the resultant mixture, 0.159 ml of 0.1M calcium chloride was then added with vigorous mixing to form aminoglycoside cochleates. In order to make particle size of the aminoglycoside cochleate crystals smaller, 20.4 mg bile salts were then added to the mixture of the aminoglycoside cochleates. The mixture was then adjusted to a drug concentration of the aminoglycoside at 0.5 mg/ml with the buffer as the suspension. The final aminoglycoside cochleate formulations contained 11.3 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. To the resultant mixture, 0.159 ml of 0.1M calcium chloride was then added with vigorous mixing to form aminoglycoside cochleates. In order to make particle size of the aminoglycoside cochleate crystals smaller, 13.6 mg bile salts were then added to the mixture of the aminoglycoside cochleates. The mixture was then adjusted to a drug concentration of the aminoglycoside at 0.5 mg/ml with the buffer as the suspension. The final aminoglycoside cochleate formulations contained 7.8 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. To the resultant mixture, 0.159 ml of 0.1M calcium chloride was then added with vigorous mixing to form aminoglycoside cochleates. In order to make particle size of the aminoglycoside cochleate crystals smaller, 6.8 mg bile salts were then added to the mixture of the aminoglycoside cochleates. The mixture was then adjusted to a drug concentration of the aminoglycoside at 0.5 mg/ml with the buffer as the suspension. The final aminoglycoside cochleate formulations contained 3.9 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. To the resultant mixture, 0.159 ml of 0.1M calcium chloride was then added with vigorous mixing to form aminoglycoside cochleates. In order to make particle size of the aminoglycoside cochleate crystals smaller, 3.4 mg bile salts were then added to the mixture of the aminoglycoside cochleates. The mixture was then adjusted to a drug concentration of the aminoglycoside at 0.5 mg/ml with the buffer as the suspension. The final aminoglycoside cochleate formulations contained 1.95 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. To the resultant mixture, 0.159 ml of 0.1M calcium chloride was then added with vigorous mixing to form aminoglycoside cochleates. In order to make particle size of the aminoglycoside cochleate crystals smaller, 1.7 mg bile salts were then added to the mixture of the aminoglycoside cochleates. The mixture was then adjusted to a drug concentration of the aminoglycoside at 0.5 mg/ml with the buffer as the suspension. The final aminoglycoside cochleate formulations contained 0.97 mM.

10.2 Procedure of aminoglycoside formulation with bile salts (before calcium) for in vitro studies.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. In order to make particle size of the aminoglycoside cochleate crystals smaller, 20.4 mg bile salts were then added to the mixture of the aminoglycoside liposomes. To the resultant mixture, 0.159 ml of 0.1M calcium chloride was then added with vigorous mixing to form aminoglycoside cochleates. The mixture was then adjusted to a drug concentration of the aminoglycoside at 0.5 mg/ml with same the buffer as the suspension. The final aminoglycoside cochleate formulations contained 11.3 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. In order to make particle size of the aminoglycoside cochleate crystals smaller, 13.6 mg bile salts were then added to the mixture of the aminoglycoside liposomes. To the resultant mixture, 0.159 ml of 0.1M calcium chloride was then added with vigorous mixing to form aminoglycoside cochleates. The mixture was then adjusted to a drug concentration of the aminoglycoside at 0.5 mg/ml with the buffer as the suspension. The final aminoglycoside cochleate formulations contained 7.8 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. In order to make particle size of the aminoglycoside cochleate crystals smaller, 6.8 μmg bile salts were then added to the mixture of the aminoglycoside liposomes. To the resultant mixture, 0.159 ml of 0.1M calcium chloride was then added with vigorous mixing to form aminoglycoside cochleates. The mixture was then adjusted to a drug concentration of the aminoglycoside at 0.5 mg/ml with the buffer as the suspension. The final aminoglycoside cochleate formulations contained 3.9 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. In order to make particle size of the aminoglycoside cochleate crystals smaller, 3.4 mg bile salts were then added to the mixture of the aminoglycoside liposomes. To the resultant mixture, 0.159 ml of 0.1M calcium chloride was then added with vigorous mixing to form aminoglycoside cochleates. The mixture was then adjusted to a drug concentration of the aminoglycoside at 0.5 mg/ml with the buffer as the suspension. The final aminoglycoside cochleate formulations contained 1.95 mM.

Aminoglycoside, 2 mg in 0.2 ml sterile water was filtered through a 0.22 μm filter and combined with 20 mg of 50% soy PS liposome in 2.0 ml sterile water (the soy PS liposome was first filtered through 5, 0.8 and 0.45 μm filters) to form liposomes containing the aminoglycoside. In order to make particle size of the aminoglycoside cochleate crystals smaller, 1.7 mg bile salts were then added to the mixture of the aminoglycoside liposomes. To the resultant mixture, 0.159 ml of 0.1M calcium chloride was then added with vigorous mixing to form aminoglycoside cochleates. The mixture was then adjusted to a drug concentration of the aminoglycoside at 0.5 mg/ml with the buffer as the suspension. The final aminoglycoside cochleate formulations contained 0.97 mM.

FIGS. 5-11 show encochleation efficiency of aminoglycoside bile salts, including amikacin bile salts, gentamycin bile salts, and paromomycin bile salts.

Encochleation percentage is determined by measuring the amount of aminoglycoside bile salts in the supernatant (ninhydrin assay) after forming the cochleates and then centrifuging. The amount in the supernatant is then subtracted from the total amount during the encochleation process. These results clearly demonstrate that 50% soy PS is more efficient at encochleating at lower bile salt concentrations than 75% PS or 99.99% PS. A is bile salts added after the encochleation. B is bile salts added before the encochleation.

What is claimed is:

1. A method for preparing cochleates comprising:
   (a) providing a suspension of liposomes in an aqueous medium, wherein the liposomes comprise (i) a lipid bilayer comprising soy phosphatidylserine in an amount of about 40%-55% by weight of the lipid bilayer, and (ii) a bioactive drug;
   (b) contacting the suspension of liposomes of (a) with a multivalent cation,
   thereby preparing cochleates.

2. The method of claim 1 wherein the lipid bilayer comprises about 45%-55% by weight soy phosphatidylserine.

3. The method of claim 1 wherein step (a), the aqueous medium containing the suspension of liposome is a buffered environment having a pH of 6.5-7.5, and the the bioactive drug is at pH 10 or higher prior to addition to the liposomes.

4. The method of claim 3 wherein the suspension of liposomes is buffered with phosphate.

5. The method of claim 1 wherein the bioactive drug is at least one member selected from the group consisting of a protein, a small peptide, a polynucleotide, an antiviral agent, an anesthetic, an antibiotic, an antifungal agent, an anticancer agent, an immunosuppressant, a steroidal anti-inflammatory agent, a non-steroidal anti-inflammatory agent, a tranquilizer, a nutritional supplement, an herbal product, a vitamin and a vasodilatory agent.

6. The method of claim 5 wherein the bioactive drug is at least one member selected from the group consisting of an aminoglycoside, amphotericin B, acyclovir, adriamycin, cabamazepine, curcumin, melphalan, nifedipine, indomethacin, naproxen, estrogens, testosterones, steroids, phenytoin, ergotamines, cannabinoids, rapamycin, propanidid, propofol, alphadione, echinomycine, miconazole nitrate, teniposide, a taxane, paclitaxel, and taxotere.

7. The method of claim 1 wherein the multivalent cation is Ca++, Zn++, Ba++, Mg++.

8. The method of claim 7 wherein the multivalent cation is Ca++.

9. The method of claim 1, wherein the bioactive drug is amphotericin B.

10. The method claim 1, wherein the bioactive drug is curcumin.

11. The method of claim 1, wherein the bioactive drug is amikacin.

12. The method claim 1, wherein weight ratio of the lipid bilayer to the bioactive drug is between about 3:1 and about 20:1.

13. The method claim 1 wherein the method further comprises a step of adding bile salts to the suspension of liposomes of (a) before step (b) or adding bile salts to the cochleates after step (b), wherein the weight ratio of the lipid bilayer to the bile salts is between 20:1 and 0.5:1.

* * * * *

UNITED STATES PATENT AND TRADEMARK OFFICE
CERTIFICATE OF CORRECTION

| | | |
|---|---|---|
| PATENT NO. | : 11,964,019 B2 | Page 1 of 1 |
| APPLICATION NO. | : 16/904824 | |
| DATED | : April 23, 2024 | |
| INVENTOR(S) | : Raphael Mannino et al. | |

It is certified that error appears in the above-identified patent and that said Letters Patent is hereby corrected as shown below:

In the Claims

In Claim 16, Column 18, Line 11, please delete "and the the bioactive" and insert -- and the bioactive --

Signed and Sealed this
Fourth Day of June, 2024

Katherine Kelly Vidal
*Director of the United States Patent and Trademark Office*